United States Patent [19]

Antons et al.

[11] Patent Number: 5,536,879
[45] Date of Patent: Jul. 16, 1996

[54] PROCESS FOR PREPARING OPTICALLY ACTIVE AMINO ALCOHOLS

[75] Inventors: Stefan Antons, Leverkusen; Bernhard Beitzke, Rösrath, both of Germany

[73] Assignee: Bayer Aktiengesellschaft, Leverkusen, Germany

[21] Appl. No.: 510,157

[22] Filed: Aug. 2, 1995

[30] Foreign Application Priority Data

Aug. 9, 1994 [DE] Germany ............... 44 28 106.4

[51] Int. Cl.$^6$ ................... C07C 209/68
[52] U.S. Cl. ............... 564/503; 564/355; 564/358; 564/453
[58] Field of Search .................. 564/355, 358, 564/453, 503

[56] References Cited

U.S. PATENT DOCUMENTS 4,058,642  11/1977  Renth et al. ............... 424/330

FOREIGN PATENT DOCUMENTS 4232505  3/1994  Germany .
9407841  4/1994  WIPO .

OTHER PUBLICATIONS

H. Adkins, et al., J. Am. Chem. Soc., vol. 69, pp. 3039–3041, (1947).
H. S. Broadbent, et al., J. Org. Chem., vol. 24, pp. 1847–1854, (1959).
E. Segel, J. Am. Chem. Soc., vol. 74, No. 4, p. 1096, (1952).
A. Abiko, et al., Tetrahedron Letters, vol. 33, No. 38, pp. 5517–5518, (1992).
R. Luckenbach, Beilsteins Handbuch der Organischen Chemie, Viertes, Ergänzungswerk, vol. IV, pp. 1797–1798, Springer–Verlag New York, (1979).
P. Karrer, et al., Helvetica Chimica Acta, vol. 31, pp. 1617–1623, (1948).
H. Seki, et al., Chem. Pharm. Bull., vol. 13, No. 8, pp. 995–1000, (1965).
H. C. Brown, et al., J. Am. Chem. Soc., vol. 78, pp. 2582–2588, (1956).
H. Adkins, et al., J. Am. Chem. Soc., vol. 69, pp. 3039–3041, (1947).
Houben–Weyl, Methoden der Org. Chemie, 4th Ed., vol. VI/1b, pp. 103–107, 206 and 214. (1987).
H. Adkins, et al., J. Am. Chem. Soc., vol. 70, pp. 3121–3125, (1948).
H. Smith Broadbent, et al., J. Org. Chem., vol. 24, pp. 1847–1854, (1959).

*Primary Examiner*—Peter O'Sullivan
*Attorney, Agent, or Firm*—Sprung Horn Kramer & Woods

[57] ABSTRACT

Optically active amino alcohols are prepared by reducing optically active amino acids with hydrogen in the presence of ruthenium catalysts.

11 Claims, No Drawings

PROCESS FOR PREPARING OPTICALLY ACTIVE AMINO ALCOHOLS

The present invention relates to a process for preparing optically active amino alcohols by reduction of the corresponding amino acids. It is known that optically active amino alcohols can be prepared by reducing the corresponding amino acids using $LiAlH_4$ in ethers (see Helv. Chim. Acta 31, 1617 (1948)). Owing to its hazardous nature, $LiAlH_4$ is not suitable for use on an industrial scale, but only for laboratory batches.

The less hazardous $NaBH_4$ reduces only amino acid esters (see Chem. & Pharm. Bull. 13, 995 (1965)). This means additional synthesis steps or special measures for activating $NaBH_4$ (see, for example, JACS 78, 2582 (1956)). The handling of $NaBH_4$ is still difficult and therefore not well suited for work on an industrial scale.

Attempts have already been made to catalytically hydrogenate carboxylic acids and esters (see Houben-Weyl, Methoden der org. Chemie, 4th edition, volume VI/1b, p. 103ff). These processes require very high pressures and temperatures. These processes are not suitable for the preparation of optically active amino alcohols, since racemizations and degradation reactions occur under these reaction conditions.

Although the catalytic reduction using rhenium oxide can be carried out at low temperatures, when amino acids are used there occurs not only a reduction of the COOH group, but also a hydrogenolytic deamination (see Examples 39 and 40 in J. Org. Chem. 24, 1847 (1959)).

Finally, the catalytic reduction using Raney nickel as catalyst is also known for the preparation of amino alcohols (see JACS 69, 3040 (1947) and 70, 3122 (1948)). However, aminocarboxylic esters have to be used as starting materials here, which means additional synthesis steps, and large amounts of the catalyst are required. Optically active amino alcohols have hitherto not been prepared in this way.

A process has now been found for preparing optically active amino alcohols, which is characterized in that optically active amino acids are reduced with hydrogen in the presence of ruthenium catalysts.

In the process of the invention it is possible, for example, to use optically active amino acids of the formula (I)

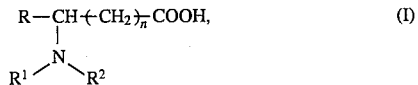

where

R represents straight-chain or branched $C_1$-$C_2$-alkyl, $C_7$-$C_2$-aralkyl or $C_6$-$C_{10}$-aryl, $R^1$ and $R^2$ represent, independently of one another, hydrogen, straight-chain or branched $C_1$-$C_{12}$-alkyl or $C_3$-$C_8$-cycloalkyl or $NR^1R^2$ represents a radical of the formula

where m=an integer from 2 to 5 or
R and $R^1$ together represent a $-(CH_2)_o-$ group where o=an integer from 2 to 6 and
n represents zero or an integer from 1 to 5,
as starting materials and obtain optically active amino alcohols of the formula (II)

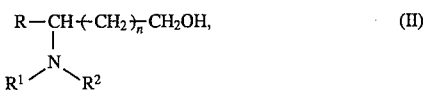

where
R, $R^1$, $R^2$ and n are as defined for formula (I).

In the process of the invention, preference is given to using optically active amino acids of the formula (I) in which R represents straight-chain or branched $C_1$-$C_4$-alkyl or benzyl, $R^1$ and $R^2$ represent, independently of one another, hydrogen, straight-chain or branched $C_1$-$C_4$-alkyl or $NR^1R^2$ represents a radical of the formula (III) where m=3 or 4 or R and $R^1$ together represent $-(CH_2)_3-$ or $-(CH_2)_4-$ and n represents zero, 1 or 2, and obtaining therefrom the corresponding optically active amino alcohols.

Suitable ruthenium catalysts are elemental ruthenium and ruthenium compounds which can both be used as such or applied to a support material. Examples of catalysts are: finely divided elemental ruthenium, ruthenium oxides, ruthenium hydroxides and ruthenium halides. Suitable support materials are, for example, carbons, aluminium oxides, silicon dioxides, silicates, alkaline earth metal carbonates and alkaline earth metal sulphates. Supported catalysts can contain, for example, from 1 to 20% by weight of elemental ruthenium or the corresponding amount of ruthenium compounds.

Based on 1 mol of optically active amino acid used, use can be made of, for example, from 0.1 to 10 g of elemental ruthenium or ruthenium compounds or from 1 to 50 g of ruthenium-containing supported catalysts.

The reduction of the invention is preferably carried out in the presence of a solvent for the optically active amino acids and optically active amino alcohols. Suitable solvents are, for example, water, water-miscible organic solvents and mixtures of the two. Water-miscible solvents which may be mentioned are lower alcohols and water-miscible ethers. Preferred solvents are water and mixtures containing water and lower alcohols or tetrahydrofuran.

Suitable reaction conditions for the reduction of the invention are, for example, temperatures in the range from 50° to 150° C. and pressures in the range from 5 to 300 bar. The reaction is preferably carried out at from 70° to 130° C. and at from 50 to 200 bar. If desired, it is also possible to proceed by commencing the reduction at a relatively low pressure, e.g. at from 50 to 150 bar, and completing it as relatively high pressures, e.g. at from 150 to 300 bar. The reaction is complete when no more hydrogen is absorbed, which is generally the case after from 10 to 50 hours.

The reaction mixture can be worked up, for example, by first cooling, separating off the catalyst, e.g. by filtration, distilling off the readily volatile constituents present (solvent and water of reaction, inter alia), optionally under slightly reduced pressure, and fractionating the residue in vacuo. The catalyst separated off can be reused, likewise the solvent.

The process of the invention can be carried out continuously or batchwise.

The surprising advantages of the process of the invention are that using the process optically active amino alcohols are obtainable in a simple manner, at relatively low temperature, with little expense and in high selectivity (enantiomeric excess ee usually above 90%).

EXAMPLE 1

A 1.3 l stainless steel autoclave was charged with 4 g of Ru black and 89 g of L-alanine in 700 g of water. After flushing with nitrogen, the autoclave was closed and pressurized with 100 bar of hydrogen. Over a period of 2 hours, the temperature was raised to 100° C. and the hydrogen pressure was increased to 200 bar. After a reaction time of 30 hours, the autoclave was cooled to room temperature and vented, the catalyst was separated from the reaction mixture by filtration and the water was distilled from the filtrate. The residue obtained was fractionally distilled under nitrogen at 10 mbar. This gave 31 g of pure L-alaninol (bp 74° C.), $[\alpha]_D^{20}=+16.9$, ee=95% (here and in the other examples determined by gas chromatography). 50 g of L-alanine remained as residue.

EXAMPLES 2 to 7

The procedure of Example 1 was repeated, but using other catalysts. Details are shown in Table 1.

TABLE 1

| Example No. | Catalyst Type | Amount (g) | ee of the alaninol obtained (%) |
| --- | --- | --- | --- |
| 2 | 10% by weight of Ru on carbon | 20 | 94 |
| 3 | $RuO_2$ | 5 | 95 |
| 4 | 5% by weight of Ru on $Al_2O_3$ | 20 | 98.5 |
| 5 | $RuO_2$ | 5 | 93 |
| 6 | 5% by weight of Ru on carbon | 20 | 97 |
| 7 | 5% by weight of Ru on carbon | 20 | 98 |

EXAMPLES 8 AND 9

The procedure of Example 1 was repeated, but using 5 g of $RuO_2$ as catalyst and employing other temperatures.

EXAMPLE 8

80° C., ee of the L-alaninol obtained 98%.

EXAMPLE 9

110° C., ee of the L-alaninol obtained 93%.

EXAMPLES 10 AND 11

In an apparatus operating continuously, 30 g/h of a 10% strength by weight aqueous solution of L-alanine were passed over 25 g of a catalyst containing 5% by weight of ruthenium on carbon at a hydrogen pressure of 200 bar. L-Alaninol was obtained at 100° C. in an ee of 92% and at 120° C. in an ee of 89 %.

EXAMPLE 12

Example 3 was repeated five times, with the catalyst separated from the preceding batch being reused each time. No change in the enantiomeric excess of the L-alaninol obtained was found.

EXAMPLES 13 TO 15

The catalyst separated off after Example 12 was introduced successively into reductions using a method similar to Example 1 but using corresponding amounts of other solvents.

EXAMPLE 13

Mixture of 80% by weight of tetrahydrofuran and 20% by weight of water, ee of the L-alaninol obtained 95%.

EXAMPLE 14

Mixture of 80% by weight of methanol and 20% by weight of water, ee of the L-alaninol obtained 94%.

EXAMPLE 15

Mixture of 80% by weight of i-propanol and 20% by weight of water, ee of the L-alaninol obtained 95%.

EXAMPLES 16 TO 18

The procedure of Example 1 was repeated, but using corresponding amounts of other amino acids. Details are shown in Table 2.

TABLE 2

| Example No. | Amino acid used Type | $[\alpha]_D^{20}$ | ee of the amino alcohol obtained (%) |
| --- | --- | --- | --- |
| 16 | L-leucine | +3.1 | 34 |
| 17 | L-valine | +16.6 | 97 |

EXAMPLE 18 (for comparison)

The procedure of Example 1 was repeated, but using 5 g of copper chromite as catalyst. No reaction took place.

When this example was repeated at higher reaction temperatures, it was found that up to 150° C. no reaction took place and at 160° C. further reaction products were formed in addition to alaninol and the alaninol is largely racemized.

EXAMPLE 19 (for comparison)

The procedure of Example 1 was repeated, but using 5 g of Raney nickel as catalyst.

It was observed that the nickel partially dissolved. Alaninol could not be isolated.

What is claimed is:

1. A process for preparing optically active amino alcohols, in which optically active amino acids are reduced with hydrogen in the presence of ruthenium catalysts.

2. The process of claim 1, in which optically active amino acids of the formula

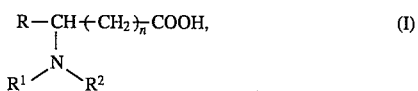

where

R represents straight-chain or branched $C_1$-$C_{12}$-alkyl, $C_7$-$C_{12}$-aralkyl or $C_6$-$C_{10}$-aryl, $R^1$ and $R^2$ represent, independently of one another, hydrogen, straight-chain or branched $C_1$-$C_{12}$-alkyl or $C_3$-$C_8$-cycloalkyl or $NR^1R^2$ represents a radical of the formula

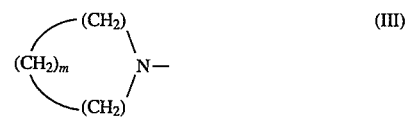

where m=an integer from 2 to 5 or

R and R¹ together represent a —(CH₂)ₒ— group where o=an integer from 2 to 6 and n represents zero or an integer from 1 to 5, are used as starting materials to give optically active amino alcohols of the formula (II)

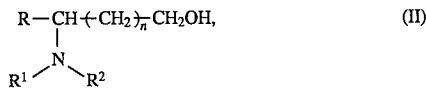

where

R, R¹, R² and n are as defined for formula (I).

3. The process of claim 1, in which the ruthenium catalyst used is selected from the group consisting of elemental ruthenium, ruthenium compounds, elemental ruthenium applied to a support material and ruthenium compounds applied to a support material.

4. The process of claim 1, in which from 0.1 to 10 g of elemental ruthenium or ruthenium compounds are used per 1 mol of optically active amino acid used.

5. The process of claim 1, in which from 1 to 50 g of ruthenium-containing supported catalyst are used per 1 mol of optically active amino acid used.

6. The process of claim 1, which is carded out in the presence of a solvent.

7. The process of claim 1, which is carried out in the presence of a solvent selected from the group consisting of water, water-miscible organic solvents and mixtures of the two.

8. The process of claim 1, which is carried out at temperatures in the range from 50° to 150° C.

9. The process of claim 1, which is carded out at pressures in the range from 5 to 300 bar.

10. The process of claim 1, in which the reaction mixture is worked up by first cooling, separating off the catalyst, distilling off the readily volatile constituents present and fractionating the residue in vacuo.

11. The process of claim 1, in which after the reaction the catalyst is separated off and reused.

* * * * *

UNITED STATES PATENT AND TRADEMARK OFFICE
CERTIFICATE OF CORRECTION

PATENT NO. : 5,536,879
DATED : July 16, 1996
INVENTOR(S) : Antons, et al.

It is certified that error appears in the above-indentified patent and that said Letters Patent is hereby corrected as shown below:

Col. 6, line 4    Delete " carded " and substitute -- carried --

Col. 6, line 12, claim 9    Delete " carded " and substitute -- carried --

Signed and Sealed this

Third Day of December, 1996

Attest:

BRUCE LEHMAN

Attesting Officer    Commissioner of Patents and Trademarks